United States Patent [19]

Öhlschläger

[11] Patent Number: 4,804,623
[45] Date of Patent: Feb. 14, 1989

[54] PHOTOGRAPHIC RECORDING MATERIAL, A PROCESS FOR THE PRODUCTION OF PHOTOGRAPHIC IMAGES AND NEW TRIAZOLES

[75] Inventor: Hans Öhlschläger, Bergisch Gladbach, Fed. Rep. of Germany

[73] Assignee: Agfa-Gevaert Aktiengesellschaft, Leverkusen, Fed. Rep. of Germany

[21] Appl. No.: 1,200

[22] Filed: Jan. 7, 1987

[30] Foreign Application Priority Data

Jan. 17, 1986 [DE] Fed. Rep. of Germany ....... 3601227

[51] Int. Cl.$^4$ .............................................. G03C 1/34
[52] U.S. Cl. ................................... 430/611; 430/551; 430/393; 548/263; 548/268
[58] Field of Search ....................... 430/611, 551, 393; 548/263, 268

[56] References Cited

U.S. PATENT DOCUMENTS 4,264,721  4/1981  Shimano et al. .................... 430/611
4,451,561  5/1984  Hirabayashi et al. ............... 430/611

*Primary Examiner*—Won H. Louie
*Attorney, Agent, or Firm*—Connolly & Hutz

[57] ABSTRACT

Improved photographic recording materials containing an antifoggant corresponding to the formula I

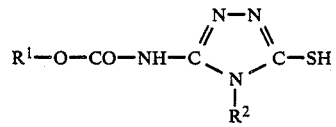

wherein the substituents have the meanings indicated in the description.

4 Claims, No Drawings

PHOTOGRAPHIC RECORDING MATERIAL, A PROCESS FOR THE PRODUCTION OF PHOTOGRAPHIC IMAGES AND NEW TRIAZOLES

This invention relates to a photographic recording material containing an antifoggant, to a process for the production of photographic images and to new triazoles.

It is well known that recording materials containing light-sensitive silver halide emulsions, especially emulsions which have been chemically sensitized, tend to fogging due to the presence of nuclei which are capable of developing without exposure to light. This fogging occurs particularly if the materials are stored for too long a time, especially at elevated temperatures and atmospheric moisture.

It is known to reduce fogging of photographic silver halide emulsions by adding so-called antifoggants or stabilizing agents, e.g. heterocyclic compounds containing sulphur, for example in the form of a mercapto group.

References may be found, for example, in German Auslegeschriften No. 1 837 371 (GB No. 1 067 066), DE No. 1 189 380 (U.S. Pat. Nos. 3,364,028 and 3,365,294), DE No. 1 597 503 (U.S. Pat. No. 3,615,617) and DE No. 1 979 027 and German Offenlegungsschriften No. 1 522 363 (GB No. 1 186 441), DE No. 2 042 533 (U.S. Pat. No. 3,761,278), DE No. 2 130 031 and DE No. 2 308 530.

It is known from DE-A-2 943 673 and U.S. Pat. No. 4,264,721 to use mercaptotriazoles substituted with an acylamino group to suppress the fog but these compounds are also liable to reduce the sensitivity of the stabilized emulsion if used in effective concentrations and when carried into the bleaching or bleach fixing bath they are liable to inhibit the bleaching process so that a fog is formed by silver which has not been removed.

It is an object of the present invention to stabilize photographic recording materials containing at least one silver halide emulsion layer against fogging, especially that which is produced under conditions of storage at elevated temperatures, without deleteriously affecting the bleaching process.

A photographic recording material containing at least one light-sensitive silver halide emulsion layer and optionally other layers and an antifoggant has now been found. According to the invention, the material contains a compound corresponding to the following formula I

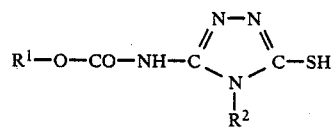

wherein
R$^1$ denotes an optionally substituted alkyl, alkenyl, cycloalkyl or aryl group and
R$^2$ denotes hydrogen or an optionally substituted alkyl or aryl group.
In a preferred embodiment,
R$^1$ denotes an optionally substituted alkyl group with 1 to 8 carbon atoms, in particular methyl, ethyl, propyl, butyl or isobutyl or an optionally substituted alkenyl group with a maximum of 5 carbon atoms, e.g. an allyl or butenyl group, or an optionally substituted cycloalkyl group with 5 or 6 ring members, e.g. cyclohexyl or methylcyclohexyl or phenyl, and
R$^2$ denotes an optionally substituted alkyl group with 1 to 4 carbon atoms, in particular methyl, ethyl, isopropyl or butyl.

The groups with which R$^1$ and R$^2$ may in turn be substituted may be any of the usual substituents used in photographic antifoggants, such as halogens, in particular chlorine or bromine, and alkoxy groups, in particular methoxy or butoxy.

There has also been found a process for the production of photographic images by imagewise exposure and processing of a photographic recording material, which process is chracterised in that a recording material according to the invention is used.

Lastly, there have been found new compounds corresponding to formula I

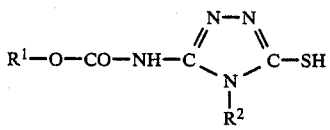

wherein the substituents have the general meanings and particularly preferred meanings indicated above.

In particularly preferred compounds according to the invention, the substituents R$^1$ and R$^2$ have the meanings shown in Table 1 below.

TABLE 1

| No. | R$^1$ | R$^2$ |
|---|---|---|
| 1 | —C$_2$H$_5$ | CH$_3$ |
| 2 | —CH(CH$_3$)$_2$ | CH$_3$ |
| 3 | 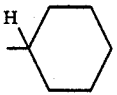 | CH$_3$ |
| 4 | —C$_2$H$_5$ | C$_2$H$_5$ |
| 5 | —CH$_2$—CH=CH$_2$ | CH$_3$ |
| 6 | —CH$_2$—CH$_2$—Cl | CH$_3$ |
| 7 | —CH$_2$—CH$_2$—CH$_2$—CH$_3$ | CH$_3$ |
| 8 | —C$_2$H$_5$ | CH$_2$—O—CH$_3$ |

The compounds according to the invention may readily be prepared by the reaction of 3-mercapto-4-alkyl-5-amino-1,2,4-triazoles with chloroformic acid esters in suitable solvents with the addition of a base such as triethylamine or sodium hydroxide.

Preparation of Compound No. 3

13 g of 3-Mercapto-4-methyl-5-amino-1,2,4-triazole were dissolved in 200 ml of acetone. 4 g of Caustic soda in 20 ml of water were added and 16.5 g of chloroformic acid cyclohexylester were then introduced dropwise with stirring and cooling at 0° to 5° C. The mixture continued to be stirred for 3 hours without further cooling and the precipitated product was suction filtered and freed from salts by washing with water. The product was then stirred up with acetone. Yield: 18.5 g of a product melting with decomposition at 194° to 195° C.

The other compounds may be prepared correspondingly.

The compounds according to the invention are advantageously added in the form of solutions, for example in solvents such as lower alcohols tetrahydrofuran, N-methylpyrrolidone or acetone.

The compounds corresponding to formula I are preferably used in quantities of from $10^{-5}$ to $10^{-2}$ mol, preferably from $10^{-4}$ to $10^{-3}$ mol per mol of silver halide.

The emulsions may also contain other antifoggants and stabilizers in combination with those used according to the invention. Particularly suitable for this purpose are the azaindenes, especially terta- and pentaazaindenes, and particularly if they are substituted with hydroxyl or amino groups. Compounds of this kind are described, for example, in the article by Birr, Z. Wiss. Phot. 47, (1952), pages 2–58. Other suitable stabilizers and antifoggants are given in Research Disclosure No. 17643 of December 1978, Section VI, published by Industrial Opportunities Limited, Homewell Havant, Hampshire, PO9 1 EF, Great Britain.

The antifoggants, including compounds of formula I to be used according to the invention, may be added to the light-sensitive silver halide emulsions before, during or after chemical ripening. In a preferred embodiment, they are added to the finished casting solution after chemical ripening.

The stabilizers are preferably added to the light-sensitive silver halide emulsions before or after chemical ripening. The stabilizers may, of course, also be added to other photographic layers associated with a silver halide emulsion layer. The concentration of stabilizers in the emulsion may vary within wide limits and depends on the nature of the emulsion and the effect to be produced. The desired effects are generally obtained with quantities of from 0.05 mmol to 50 mmol, in particular from 0.2 to 20 mmol per mol of silver halide.

The usual silver halide emulsions are suitable for the present invention. The silver halides contained in them may consist of silver chloride, silver bromide or mixtures thereof, optionally with a silver iodide content of preferably up to 10 mol-%, and the distribution of the halide may have a gradient within the grain.

The silver halide emulsions may be prepared by the conventional methods (e.g. single or double inflow with constant or accelerated delivery of substance). The process of double inflow with control of the pAg value is particularly preferred. See the above-mentioned Research Disclosure No. 17643, Sections I and II.

In a preferred embodiment, the silver halides consist predominantly of compact crystals which may, for example, have cubical, octahedric or transitional forms. They may be characterised by their thickness which is generally greater than 0.2 μm. The average ratio of diameter to thickness is preferably less than 8:1, the diameter being that of a circle having the same surface area as the projected surface of the grain. In another preferred embodiment, the silver halide crystals may be mainly tabular in all or some of the emulsions, with a ratio of diameter to thickness greater than 8:1.

The emulsions may be monodisperse with an average grain size preferably in the range of 0.3 μm to 1.1 μm. The silver halide grains may have a layered grain structure.

The emulsions are preferably chemically sensitized to a high surface sensitivity on the surface of the grain. This chemical sensitization may be carried out by known methods, e.g. using active gelatine or compounds of sulphur, selenium, tellurium, gold, palladium, platinum or iridium, The pAg values may vary from 4 to 10, the pH values in the region of 3, 5 and 9 and the temperatures from 30° C. to 90° C. Chemical sensitization may be carried out in the presence of heterocyclic nitrogen compounds such as immidazoles, azaindenes, azapyridazines and azapyrimidines, thiocyanate derivatives, thioethers and other silver halide solvents. Instead of or in addition to this sensitization, the emulsions according to the invention may be subjected to a reduction sensitization, e.g. by means of hydrogen, by a low pAg value (e.g. below 5), and/or by the pH value (e.g. above 8) or by means of reducing agents such as tin(II) chloride, thiourea dioxide or aminoboranes.

The surface-ripened nuclei may also be present as troglodyte nuclei (sub-surface nuclei) according to DE-OS No. 2 306 447 and U.S. Pat. No. 3,966,476. Other methods are described in the above mentioned Research Disclosure No. 17643, Section III.

The emulsions may be optically sensitized in known manner, e.g. with the usual polymethine dyes such as neutrocyanines, basic or acid carbocyanines, rhodacyanines, hemicyanines, styryl dyes, oxonols and the like. Sensitizers of this kind are described by F. M. Hamer in "The Cyanine Dyes and Related Compounds", (1964). See also in particular Ullmanns Enzyklopädie der technischen Chemie, 4th Edition, Volume 18, pages 431 et seq, and the above mentioned Research Disclosure No. 17643, Section IV.

The colour photographic recording materials normally contain at least one silver halide emulsion layer unit for each of the three spectral regions, red, green and blue.

Each of the above-mentioned silver halide emulsion layer units may contain one or more silver halide emulsion layers. Colour photographic recording materials having double layers for the different spectral regions are known, for example, from U.S. Pat. Nos. 3,663,228, 3,849,138 and 4,184,876. Colour photographic recording materials having triple layers are disclosed in DT-OS No. 2 018 341 and DE No. 3 413 800.

In addition, any layer may contain formalin absorbents such as the iminopyrazolones disclosed in DE-A-3 148 108 and U.S. Pat. No. 4,414,309.

The material preferably has at least one blue-sensitive layer placed above the green- and red-sensitive layers and separated from these layers by a yellow filter layer. Protective and intermediate layers may be used in addition to the light-sensitive layers.

In addition to the layers already mentioned above, light-insensitive auxiliary layers may be present in the colour photographic recording material according to the invention, e.g. bonding layers, antihalation layers and covering layers, in particular interlayers placed between light-sensitive layers to prevent diffusion of developer oxidation products from one layer to another. For this purpose, such interlayers may contain certain compounds capable of reacting with developer oxidation products. Layers of this kind are preferably arranged between adjacent light-sensitive layers which differ in their spectral sensitivities. Interlayers may also be used to incorporate a low sensitivity silver halide emulsion having an average grain diameter of about 0.8 μm or less and containing chloride, bromide and optionally iodide. A layer of this kind has a particularly advantageous effect on the sensitivity of the adjacent layers but the low sensitivity silver halide emulsion may also be directly incorporated in the light-sensitive layers.

The layers may in addition contain the usual components such as scavengers, DIR couplers and DAR couplers.

The light-sensitive silver halide emulsion layers preferably have colour couplers associated with them which are capable of reacting with colour developer oxidation products to form a dye. The colour couplers are preferably directly adjacent to the silver halide emulsion layer or better still contained in the silver halide emulsion layer itself.

Thus, the red-sensitive layer, for example, may contain a colour coupler for producing the cyan partial colour image, generally a coupler of the phenol or α-naphthol series. The green-sensitive layer, for example, may contain at least one colour coupler for producing the magenta partial colour image, usually a colour coupler of the 5-pyrazolone series. The blue-sensitive layer, for example, may contain at least one colour coupler for producing the yellow partial colour image, generally a colour coupler containing an open chain ketomethylene group.

The colour couplers may be, for example, 6-, 4- or 2-equivalent couplers. Suitable couplers have been disclosed, for example, in the publication entitled "Farbkuppler" by W. Pelz in "Mitteilungen aus den Forschungslaboratorien der Agfa, Leverkusen/München", Volume III, page 111 (1961); by K. Venkataraman in "The Chemistry of Synthetic Dyes", Vol. 4, 341 to 387, Academic Press (1971) and by T. H. James, in "The Theory of the Photographic Process", 4th Edition, pages 353–362, as well as in Research Disclosure No. 17643 of December 1978, Section VII, published by Industrial Opportunities Ltd., Homewell Havant, Hampshire, PO9 1 EF, Great Britain.

The usual masking couplers may be used to improve the colour reproduction. In addition, the recording material may contain DIR conpounds and white couplers which do not yield a dye when they reach with colour developer oxidation products. Inhibitors may be split off from the DIR compounds either directly or with non-inhibitory intermediate compounds.

See GB No. 953 454, U.S. Pat. No. 3,632,345, U.S. Pat. No. 4 248 962 and GB No. 2 072 363 and Research Disclosure No. 10226 of October 1972.

Examples of particularly suitable yellow couplers are shown in the Table below.

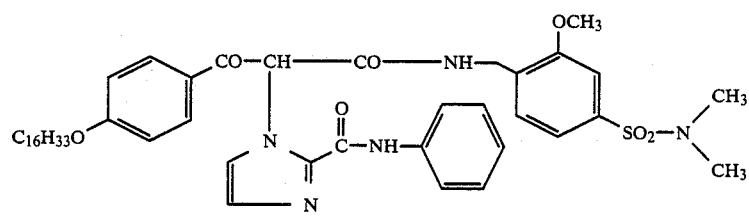

Y 1

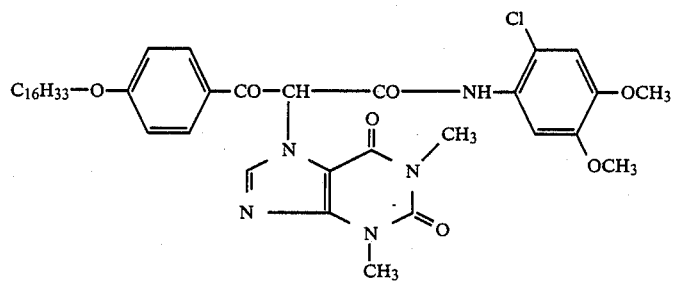

Y 2

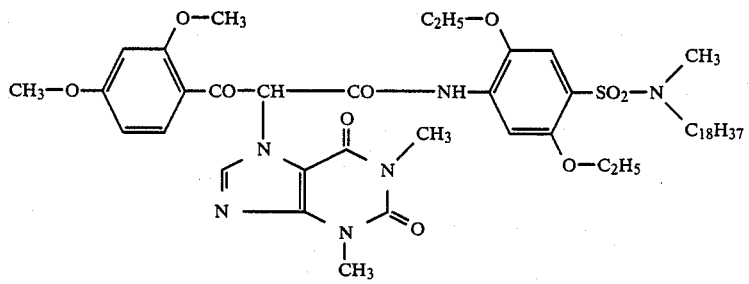

Y 3

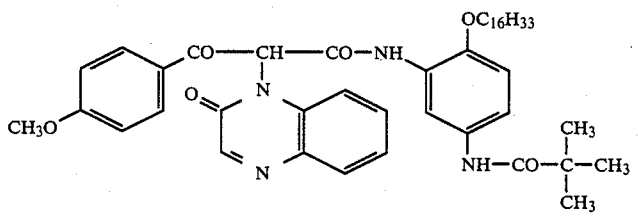

Y 4

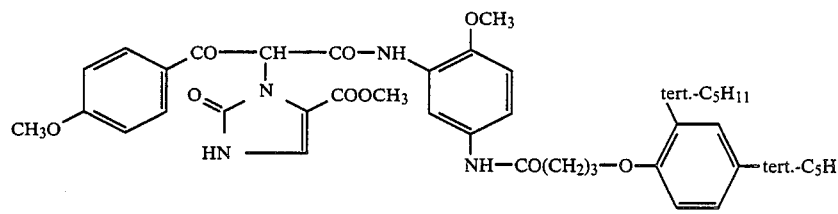
Y 5
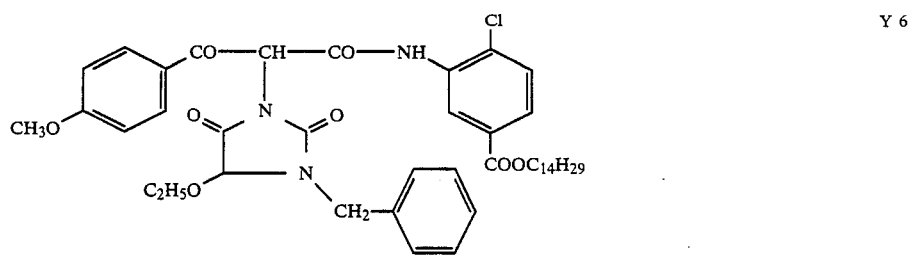
Y 6
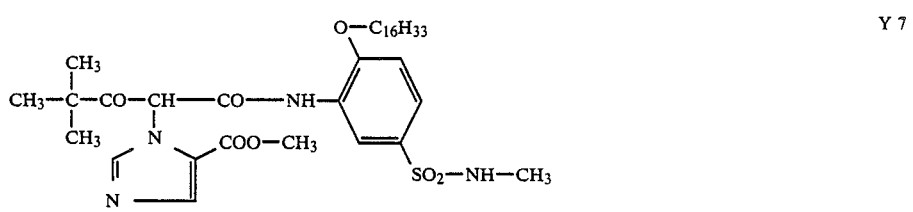
Y 7
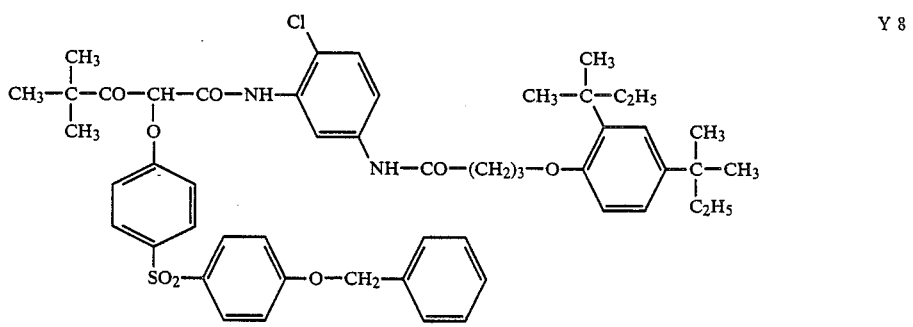
Y 8
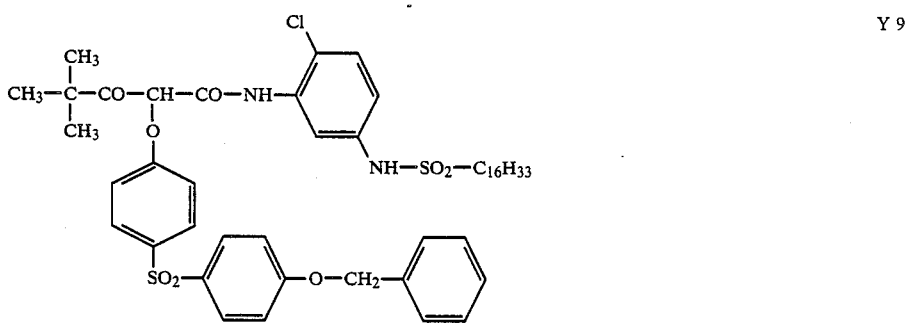
Y 9
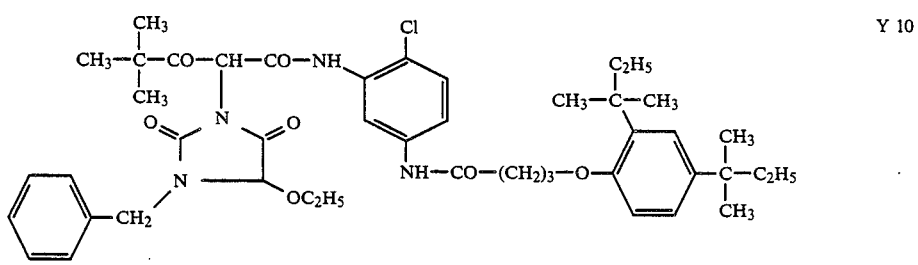
Y 10

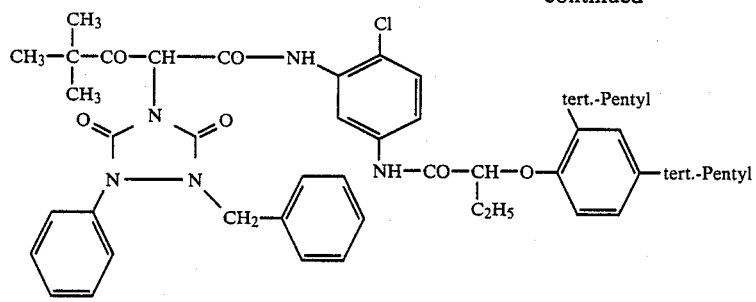
Y 11
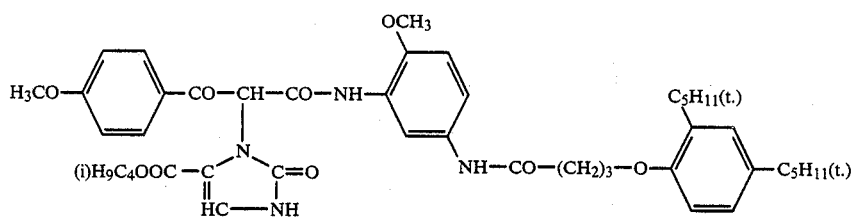
Y 12
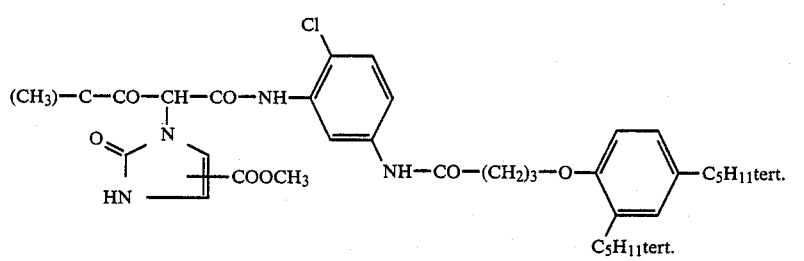
Y 13
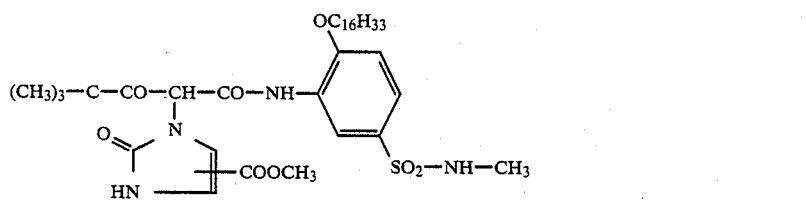
Y 14
Examples of exceptionally suitable cyan couplers are shown in the Table below.
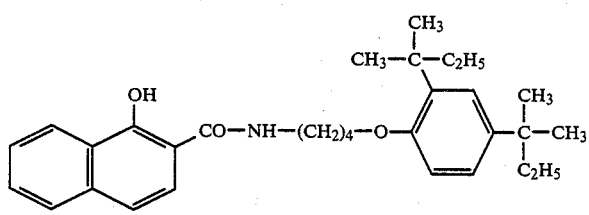
C 1
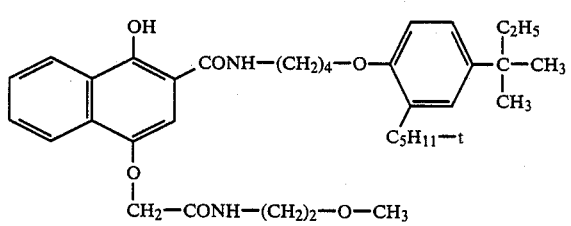
C 2

-continued
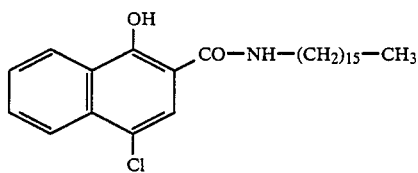 C3
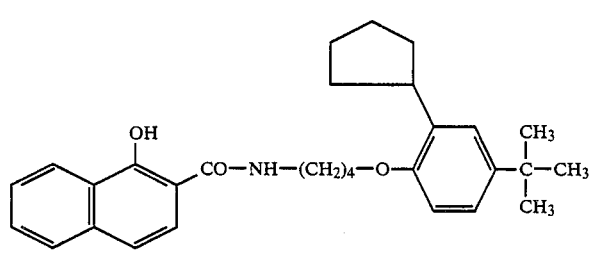 C4
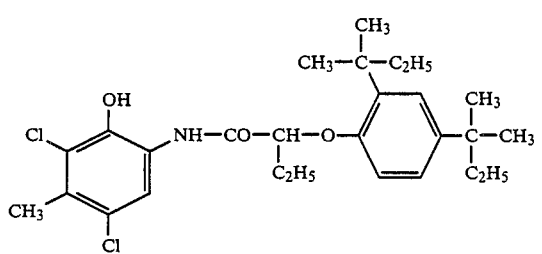 C5
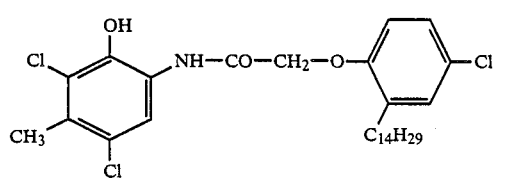 C6
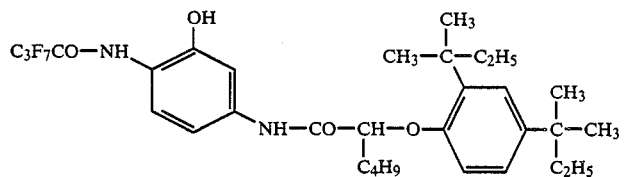 C7
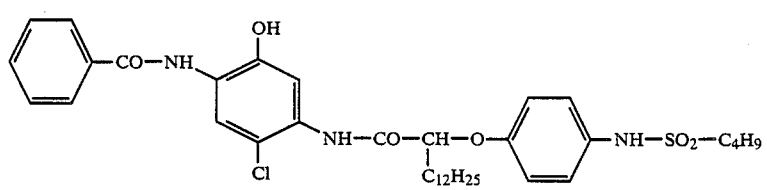 C8
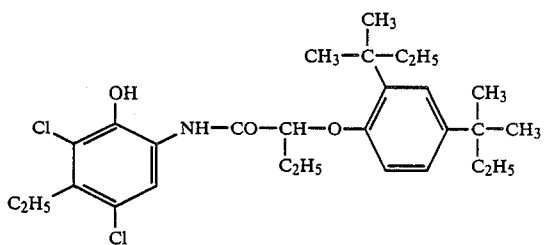 C9

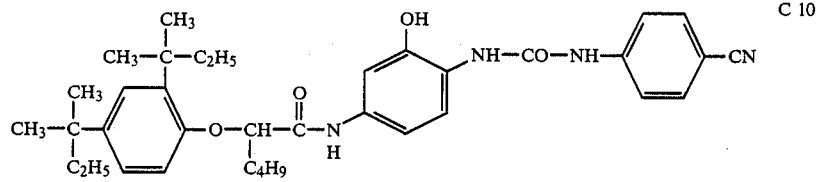
C 10
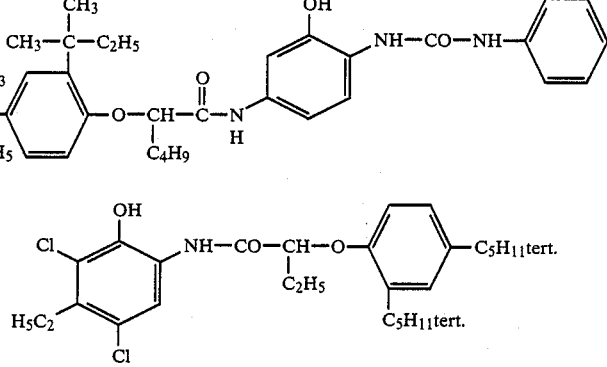
C 11
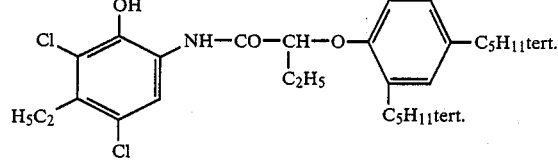
C 12
The following compounds are used as magenta couplers:
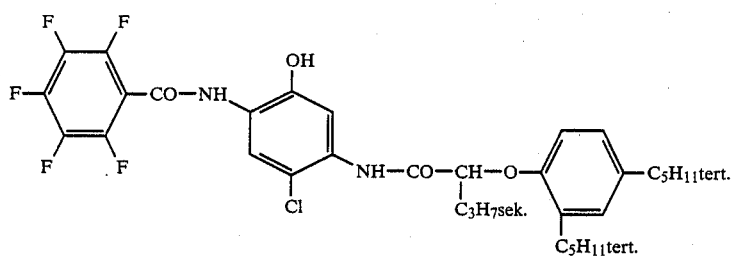
Pp 1
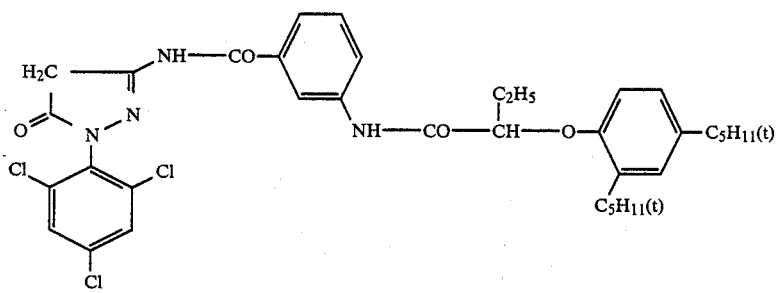
Pp 2
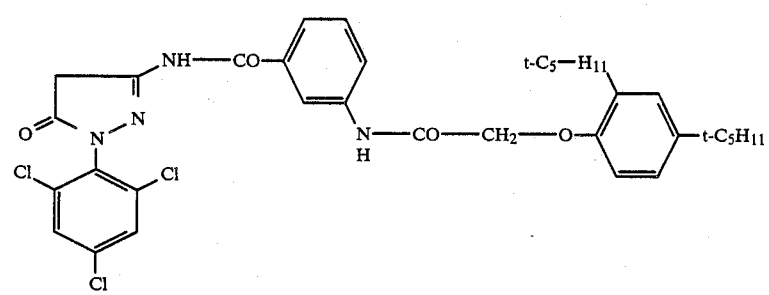
Pp 3
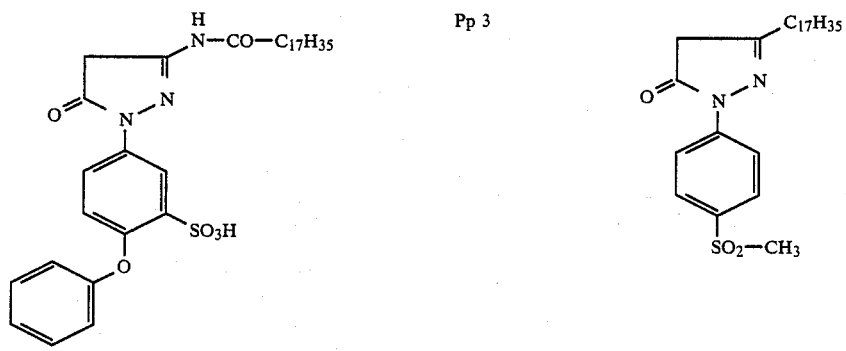
Pp 4

-continued
Pp 5
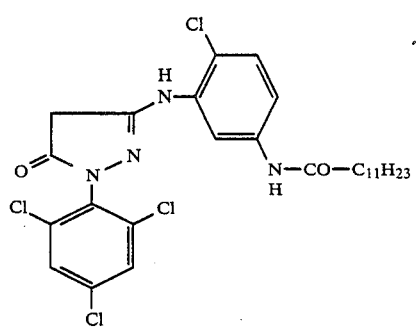
Pp 6
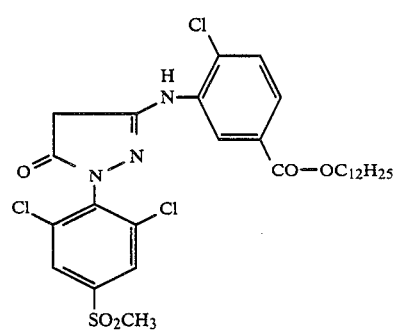
Pp 7
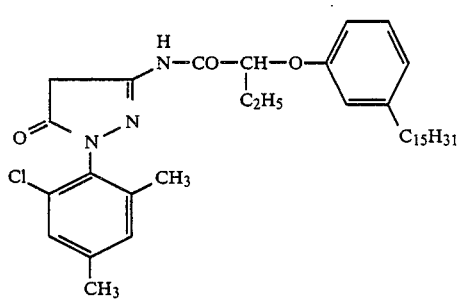
Pp 8
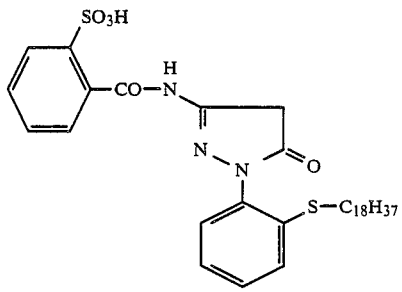
Pp 9
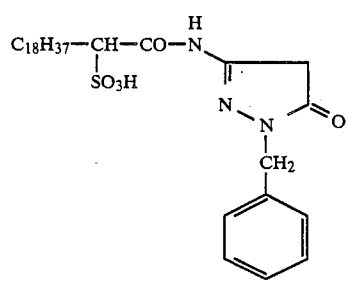
Pp 10
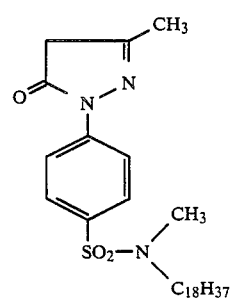
Pp 11
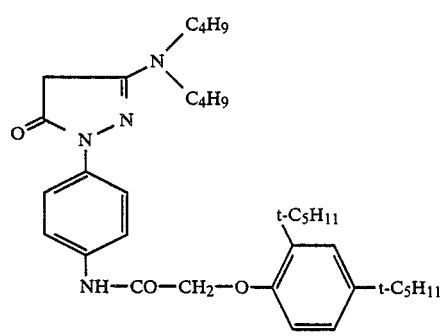
Pp 12
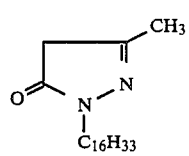
Pp 13
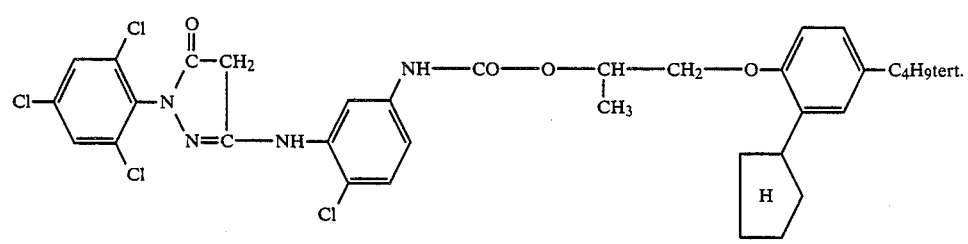

-continued
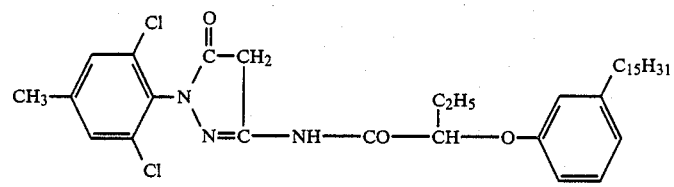
Pp 14
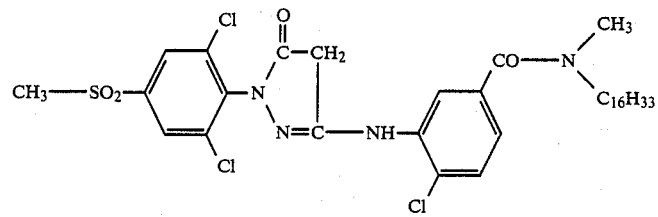
Pp 15
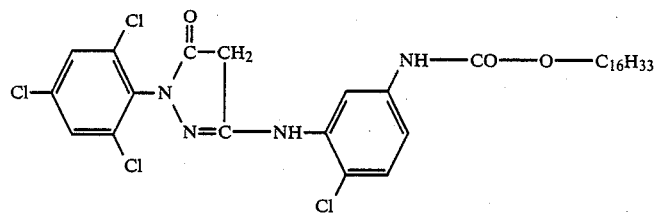
Pp 16
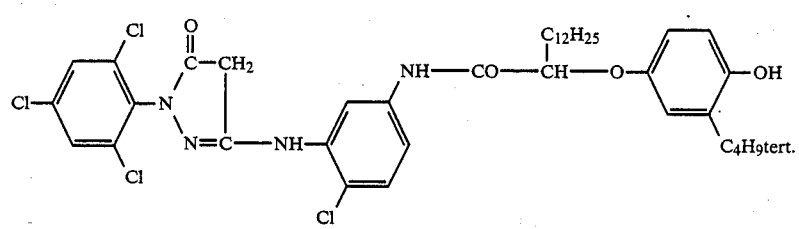
Pp 17
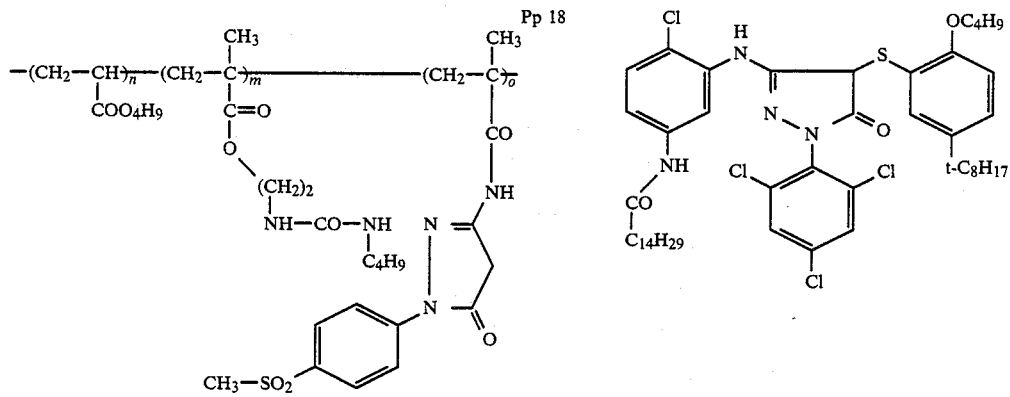
Pp 18 / Pp 19
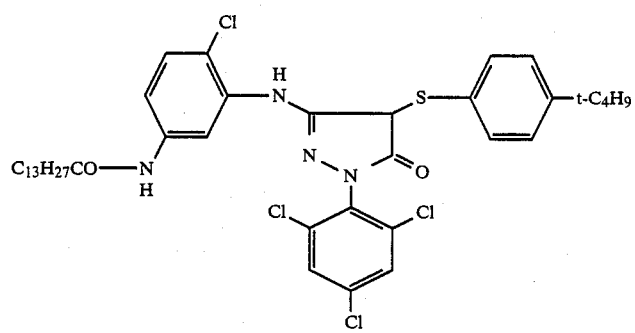
Pp 20

-continued
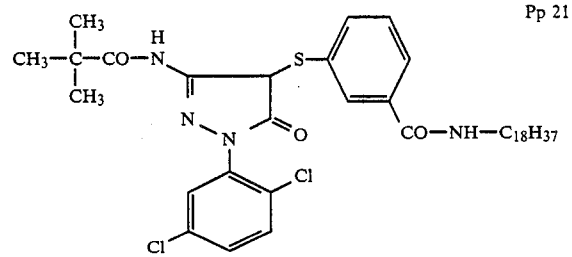 Pp 21
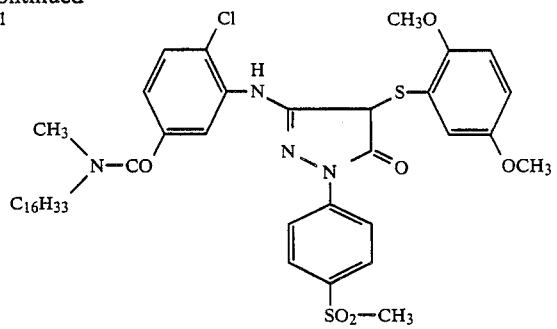 Pp 22
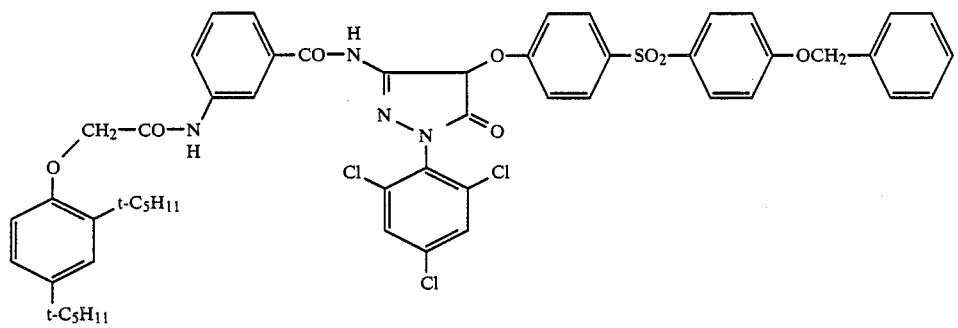 Pp 23
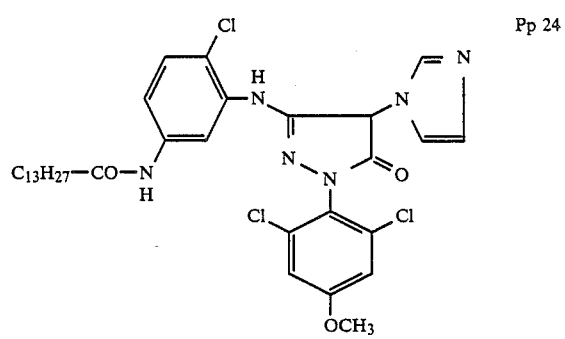 Pp 24
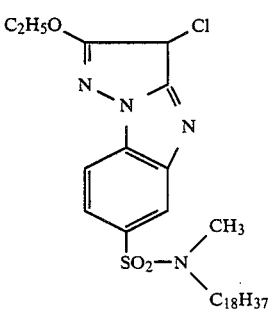 Pp 25
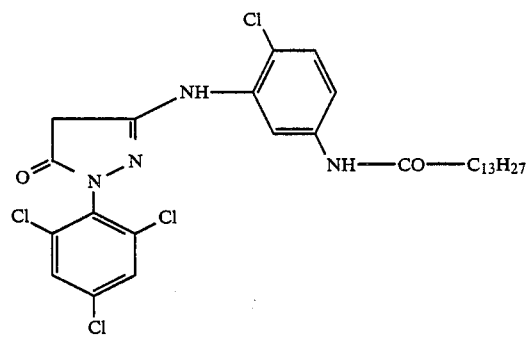 Pp 26
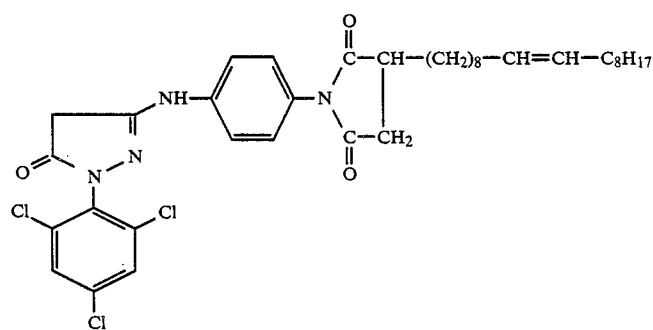 Pp 27

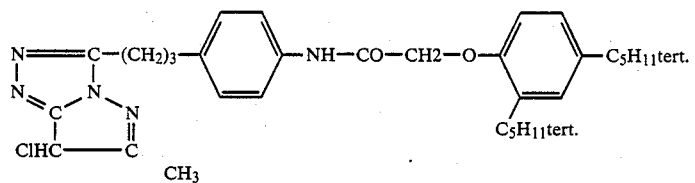
Pp 28

Suitable masking couplers are shown below:

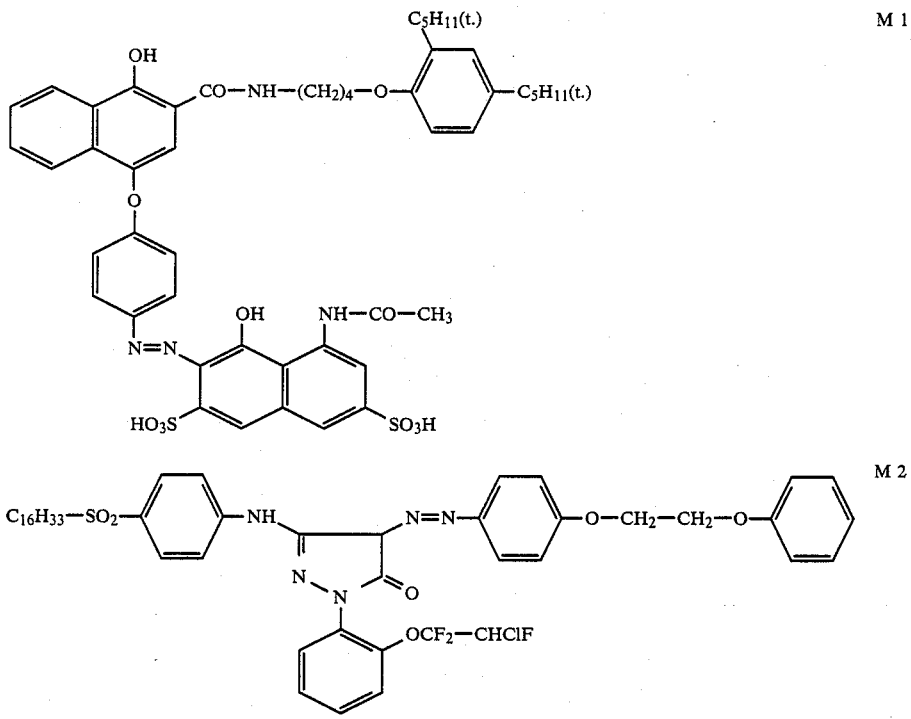

M 1

M 2

The following are examples of structures of suitable DIR couplers:

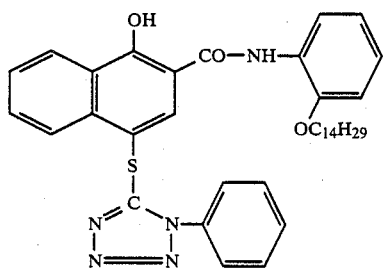
DIR 1

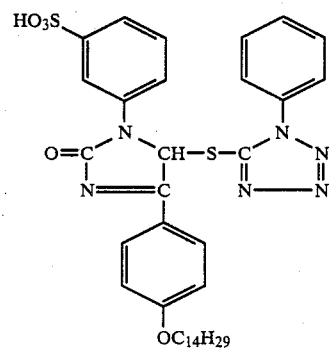
DIR 2

The components of the photographic material may be incorporated by the usual, known methods. If they consist of water-soluble or alkali-soluble compounds, they may be added in the form of aqueous solutions, optionally with the addition of water-miscible organic solvents such as ethanol, acetone or dimethylformamide. If they are insoluble in water and in alkalies, they may be incorporated in the recording materials in the form of dispersions in known manner. For example, a solution of these compounds in a low boiling organic solvent may be directly mixed with the silver halide emulsion or it may first be mixed with an aqueous gelatine solution from which the organic solvent is subsequently removed and the resulting dispersion of the required compound may then be mixed with the silver halide emulsion. So-called oil formers may also be used. These are generaly relatively high boiling organic compounds which form oily droplets enclosing the compounds to be dispersed.

See in this connection, for example, U.S. Pat. Nos. 2,322,027, 2,533,514, 3,689,271, 3,764,336 and 3,765,897. Couplers may also be incorporated, for example, in the form of charged latices, see DE-OS No. 2 541 274 and EP-A No. 14 921. The components may also be fixed in the material as polymers, see e.g. DE-OS No. 2 044 992, U.S. Pat. No. 3,370,952 and U.S. Pat. No. 4,080,211.

The usual layer supports may be used for the materials according to the invention, see Research Disclosure No. 17643, Section XVII.

The usual hydrophilic film-forming agents may be used as protective colloids or binders for the layers of the recording material, e.g. proteins, in particular gelatine. Casting auxiliaries and plasticizers may also be used; see the compounds mentioned in the above Research Disclosure No. 17643, Sections IX, XI and XII.

The layers of the photographic material may be hardened in the usual manner, for example with hardeners of the type of epoxides, heterocyclic ethyleneimines or acryloyls. The layers may also be hardened by the process according to German Offenlegungsschrift No. 2 218 009 to produce colour photographic materials suitable for high temperature processing. Furthermore, the photographic layers may be hardened with hardeners of the diazine, triazine or 1,2-dihydroquinoline series or with hardeners of the vinyl sulphone type. Other suitable hardeners are disclosed in German offenlegungsschrifte Nos. 2 439 551, 2 225 230 and 2 317 672 and the above mentioned Research Disclosure 17 643, Section XI.

Other suitable additives are mentioned in Research Disclosure 17 643 and in "Product Licensing Index" of December 1971, pages 107–110.

Suitable colour developer substances for the material according to the invention include in particular those of the p-phenylenediamine series, e.g. 4-amino-N,N-diethylaniline hydrochloride; 4-amino-3-methyl-N-ethyl-N-$\beta$-(methane sulphonamido)-ethylaniline sulphate hydrate; 4-amino-3-methyl-N-ethyl-N-$\beta$-hydroxyethylaniline sulphate; 4-amino-N-ethyl-N-(2-methoxyethyl)-m-toluidine-di-p-toluene sulphonic acid and N-ethyl-N-$\beta$-hydroxyethyl-p-phenylenediamine. Other suitable colour developers are described, for example, in J. Amer. Chem. Soc. 73, 3100 (1951) and by G. Haist in Modern Photographic Processing, 1979, John Wiley and Sons, New York, pages 545 et seq.

After colour development, the material is bleached and fixed in the usual manner. Bleaching and fixing may be carried out either separately or together. The usual bleaching agents may be used, e.g. $Fe^{3+}$ salts and $Fe^{3+}$ complex salts such as ferricyanides, dichromates, water-soluble cobalt complexes, etc. Iron-III complexes of aminopolycarboxylic acids are particularly preferred, e.g. ethylene diaminotetracetic acid, nitrilotriacetic acid, iminodiacetic acid, N-hydroxyethyl-ethylenediaminotriacetic acid, alkyliminodicarboxylic acids and corresponding phosphonic acids. Persulphates are also suitable bleaching agents.

The examples which follow, in which preferred embodiments of the invention are described, serve to explain the invention in more detail. Unless otherwise indicated, percentages are percentages by weight and quantities refer to the amount applied per m² of recording material. The quantity of silver halide applied is given in terms of the equimolar quantity of silver nitrate.

EXAMPLE 1

A high sensitivity silver iodobromide emulsion containing 5 mol-% of iodide and 150 g of silver nitrate per kg of emulsion and having a gelatine:silver ratio of 1.2 was ripened to optimum sensitivity with silver and gold compounds.

The formulation for the emulsion was divided into several parts and the following substances were added per kg of emulsion:

| | |
|---|---|
| 4-Hydroxy-6-methyl-1,3,3a,7-tetraazaindene 1%, aqueous alkaline solution | 1,500 mg |
| Saponin 10%, dissolved in water | 3.5 g | and the substances according to the invention shown in the following Table (1% solutions in N-methylpyrrolidone/methanol 1:10) in the quantities indicated. The quantities were calculated to ensure that no significant loss in sensitivity occurred.

The emulsions were then cast on a cellulose acetate support and dried (application 6.7 to 7.0 g, calculated as silver nitrate per m²). Each emulsion layer was covered with a protective layer containing a hardener corresponding to the formula

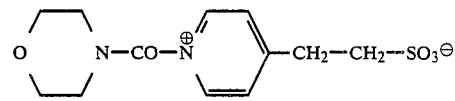

and a wetting agent, the protective layer containing 2 g of gelatine per m².

The samples were then exposed behind a grey wedge in a sensitometer and developed for 7 minutes at 20° C. in a developer (I) having the following composition:

Developer I

| | |
|---|---|
| p-methylaminophenol | 3.5 g |
| Hydroquinone | 3.5 g |
| Sodium sulphite sicc. | 70.0 g |
| Sodium carbonate sicc. | 40.0 g |
| Potassium bromide | 2.0 g |
| Borax | 7.0 g |
| made up with water to 1000 ml. | |

The samples were then fixed in an acid fixing bath in the usual manner and rinsed. The results of the sensitometric tests are summarized in Table 2 below. The Table shows that the substances reduce fogging and are therefore suitable as antifoggants even when the material is stored at elevated temperatures or moisture.

TABLE 2

| Compound | Quantity Mol/Mol $AgNO_3$ | $S_F$ | $F_F$ | $S_H$ | $F_H$ | $S_T$ | $F_T$ |
|---|---|---|---|---|---|---|---|
| Control | — | 29.9 | 0.19 | 29.5 | 0.20 | 29.5 | 0.18 |
| 1 | $1.7 \cdot 10^{-4}$ | 29.3 | 0.10 | 28.9 | 0.11 | 29.2 | 0.09 |
| 1 | $3.4 \cdot 10^{-4}$ | 29.1 | 0.07 | 28.1 | 0.06 | 28.9 | 0.05 |
| 2 | $1.7 \cdot 10^{-4}$ | 29.6 | 0.06 | 28.8 | 0.06 | 29.1 | 0.05 |
| 2 | $3.4 \cdot 10^{-4}$ | 29.5 | 0.04 | 29.0 | 0.04 | 29.3 | 0.04 |
| 3 | $1.7 \cdot 10^{-4}$ | 29.8 | 0.06 | 29.4 | 0.06 | 29.2 | 0.05 |

TABLE 2-continued

| Compound | Quantity Mol/Mol AgNO$_3$ | $S_F$ | $F_F$ | $S_H$ | $F_H$ | $S_T$ | $F_T$ |
|---|---|---|---|---|---|---|---|
| 3 | 3.4 · 10$^{-4}$ | 29.4 | 0.04 | 28.7 | 0.04 | 29.0 | 0.04 |
| 5 | 1.7 · 10$^{-4}$ | 29.9 | 0.10 | 29.5 | 0.10 | 29.1 | 0.09 |
| 5 | 3.4 · 10$^{-4}$ | 29.1 | 0.08 | 29.1 | 0.09 | 28.9 | 0.08 |

$S_F$, $F_F$ = Sensitivity and fog of fresh sample
$S_H$, $F_H$ = Sensitivity and fog after 3 days at 60° C./40% humidity
$S_T$, $F_T$ = Sensitivity and fog after 3 days at 35° C./80% humidity
An increase in the given numerical values by three units corresponds to a doubling of the sensitivity.

EXAMPLE 2

1.2 g of 4-Hydroxy-6-methyl-1,3,3a,7-tetraazaindene in aqueous alkaline solution was added to 1 kg of a green-sensitized iodobromide silver emulsion containing silver (calculated as silver nitrate) and gelatine in proportions of 1:0.4 with a silver halide content of 0.91 mol per kg of emulsion and an iodide content of 5 mol-%, and the resulting emulsion was divided into several equal parts. The compounds according to the invention shown in Table 3 were added as solutions in methanol to the individual samples in the quantities indicated. The following were added per kg of emulsion before casting:

75 g of a 5% gelatine solution,
109 g of an 11.1% coupler dispersion of the following magenta coupler

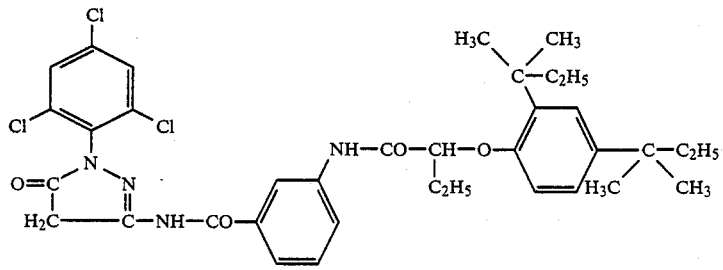

wetting agents in aqueous solution and 1180 ml of water.

The emulsions were cast on an antihalation layer consisting of silver dispersion on a cellulose acetate support. The quantity of emulsion applied in each case corresponded to a silver application of 2.2 to 2.3 g of AgNO$_3$/m$^2$.

A protective layer as described in Example 1 was applied to each emulsion layer.

The samples were tested fresh and after storage in a heating cupboard for 3 days at 60° C. and 40% relative humidity and after storage in a tropical cupboard for 3 days at 35° C. and 80% relative humidity.

The samples were then exposed behind a step wedge in a sensitometer and developed in the following developer II for 3¼ minutes at 38° C.

Developer II

| | |
|---|---|
| Sodium salt of 1-hydroxyethane-1,1-disulphonic acid | 2 g |
| Ethylene diamino-N,N,N',N'—tetracetic acid | 2 g |
| Potassium carbonate sicc. | 34.1 g |
| Sodium bicarbonate sicc. | 1.55 g |
| Sodium disulphite sicc. | 0.28 g |
| Sodium sulphite sicc. | 3.46 g |
| Potassium bromide | 1.34 g |
| Hydroxylamine sulphate | 2.4 g |
| 4-Amino-3-methyl-N—ethyl-N—(β-hydroxyethyl)-aniline | 4.7 g |
| made up with water to 1 l. | |

Subsequent processing was carried out in the following baths:

| | |
|---|---|
| Short stop bath | 1 minute at 38° C. |
| Bleaching bath | 3¼ minutes at 38° C. |
| Washing | 3½ minutes at 38° C. |
| Fixing bath | 3¼ minutes at 38° C. |
| Washing | 5 minutes at 38° C. |

Conventional short stop, bleaching and fixing baths were used (British Journal of Photography, 1974, pages 597 and 598).

The results obtained are shown in Table 3.

The substances reduce the very high fog without substantially reducing the sensitivity and gradation and they improve the storage stability of the photographic material.

By contrast, the triazole derivatives disclosed in DE-A-2 943 673 (Comparison I–II) only slightly reduce fogging and severely depress the sensitivity.

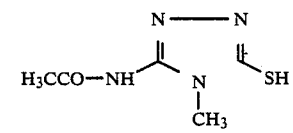

Comparison I = Compound 3 from OS 2 943 673

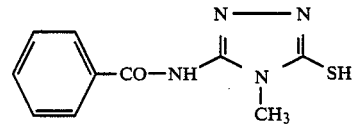

Comparison II = Compound 17 from OS 2 943 673

TABLE 3

| Compound No. | Mol/100 g AgNO$_3$ | $S_F$ | $F_F$ | $S_H$ | $F_H$ | $S_T$ | $F_T$ |
|---|---|---|---|---|---|---|---|
| Control | — | 22.9 | 0.61 | 24.0 | 0.80 | 22.3 | 0.50 |
| 1 | 1.7 · 10$^{-4}$ | 22.3 | 0.40 | 23.6 | 0.48 | 21.7 | 0.37 |
| 1 | 3.4 · 10$^{-4}$ | 21.9 | 0.32 | 22.5 | 0.32 | 21.4 | 0.31 |
| 2 | 1.7 · 10$^{-4}$ | 21.9 | 0.40 | 24.2 | 0.37 | 21.7 | 0.32 |
| 2 | 3.4 · 10$^{-4}$ | 21.7 | 0.35 | 23.9 | 0.34 | 21.1 | 0.31 |
| 3 | 1.7 · 10$^{-4}$ | 22.2 | 0.39 | 23.3 | 0.46 | 21.7 | 0.37 |
| 3 | 3.4 · 10$^{-4}$ | 22.0 | 0.39 | 22.5 | 0.40 | 21.6 | 0.35 |
| 6 | 1.7 · 10$^{-4}$ | 22.2 | 0.44 | 23.4 | 0.46 | — | 0.35 |
| 6 | 3.4 · 10$^{-4}$ | 22.0 | 0.36 | 22.4 | 0.42 | 20.4 | 0.32 |
| Compar. I | 1.7 · 10$^{-4}$ | 21.8 | 0.47 | 22.9 | 0.64 | 21.4 | 0.46 |
| Compar. I | 3.4 · 10$^{-4}$ | 20.6 | 0.46 | 21.0 | 0.54 | 20.3 | 0.44 |
| Compar. II | 1.7 · 10$^{-4}$ | 20.1 | 0.47 | 20.0 | 0.44 | 19.3 | 0.40 |

TABLE 3-continued

| Compound No. | Mol/100 g AgNO₃ | $S_F$ | $F_F$ | $S_H$ | $F_H$ | $S_T$ | $F_T$ |
|---|---|---|---|---|---|---|---|
| Compar. II | $3.4 \cdot 10^{-4}$ | 19.8 | 0.38 | 19.4 | 0.39 | 19.6 | 0.32 |

For meaning of $S_F$, $F_F$, $S_H$, $F_H$, $S_T$, $F_T$ see Table 2.

EXAMPLE 3

64 mg of 4-Hydroxy-6-methyl-1,3,3a,7-tetraazaindene were added as an aqueous alkaline solution to 1 kg of a red-sensitized silver chlorobromide emulsion containing 15 mol-% of chloride and 100 g of silver nitrate per kg and the resulting emulsion was divided into several parts. The compounds according to the invention shown in Table 4 were added as solutions in methanol to the individual samples. The following cyan coupler

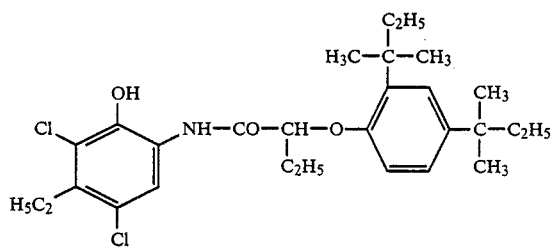

emulsified in gelatine solution using tricresyl phosphate was subsequently added, together with a wetting agent.

Each of these mixtures was applied to a substrated polyethylene coated paper in a quantity corresponding to 0.48 g of silver calculated as AgNO₃/m². A protective layer containing 1.8 g of gelatine/m² was then applied to the emulsion layer.

The layer packet was coated with a hardener as in Example 1.

The layers thus obtained were exposed behind a $\sqrt[8]{2}$ stepped wedge and a red filter and then developed as follows:

| Colour developer III | 33° C. | 3.5 minutes |
|---|---|---|
| Bleach fixing bath | 33° C. | 1.5 minutes |
| Washing | 33° C. | 3 minutes. |

The processing baths were prepared according to the following formulations:

Developer III

| 900 ml | water |
|---|---|
| 15 ml | benzyl alcohol |
| 15 ml | ethylene glycol |
| 3 g | hydroxylamine sulphate |
| 4.5 g | 3-methyl-4-amino-N—ethyl-N—(β-methanesulphonamidoethyl)-aniline sulphate |
| 32 g | potassium carbonate sicc. |
| 2 g | potassium sulphite sicc. |
| 0.6 g | potassium bromide |
| 1 g | disodium salt of 1-hydroxyethylidene-1,1-diphosphonic acid |
| | made up with water to 1 l and adjusted to pH 10.2. |

Bleach fixing bath

| 700 ml | water |
|---|---|
| 35 ml | ammonia solution (28%) |
| 30 g | ethylene diamino-N,N,N′.N′—tetracetic acid |
| 15 g | sodium sulphite sicc. |
| 100 g | ammonium thiosulphate sicc. |
| 60 g | sodium-(ethylenediaminotetraacetate)-iron-(III) complex |
| | made up with water to 1 l and adjusted to pH 7. |

The cyan colour wedges were examined after development. The numerical results obtained are shown in Table 4 below.

TABLE 4

| Compound No. | Conc. mol/ mol AgNO₃ | Sensitivity D 0.6 | D min. |
|---|---|---|---|
| Control | — | 1.95 | 0.150 |
| 1 | $1.7 \cdot 10^{-4}$ | 1.86 | 0.131 |
| 1 | $3.4 \cdot 10^{-4}$ | 1.86 | 0.133 |
| 2 | $1.7 \cdot 10^{-4}$ | 1.90 | 0.135 |
| 2 | $3.4 \cdot 10^{-4}$ | 1.92 | 0.138 |
| 4 | $1.7 \cdot 10^{-4}$ | 1.89 | 0.137 |
| 4 | $3.4 \cdot 10^{-4}$ | 1.87 | 0.129 |
| 7 | $1.7 \cdot 10^{-4}$ | 1.99 | 0.144 |
| 7 | $3.4 \cdot 10^{-4}$ | 2.09 | 0.139 |
| 8 | $1.7 \cdot 10^{-4}$ | 1.86 | 0.132 |
| 8 | $3.4 \cdot 10^{-4}$ | 1.82 | 0.118 |

EXAMPLE 4

In this example, known stabilizers containing mercapto groups are compared with the stabilizers according to the invention in their response to bleaching.

The quantity of stabilizer shown in Table 5 (mol of stabilizer per mol of silver) was added to a silver filter yellow gelatine solution and after the addition of saponin as wetting agent the resulting mixture was cast on a subtrated polyethylene-coated paper support to form layers having a density of 1.7 to 2.0 μm.

The samples were washed for 5 minutes and then bathed in a bleach fixing bath of the following composition for one minute at 20° C.:

15 g sodium salt of Fe-III complex of ethylene diamino tetracetic acid
10 g sodium sulphite sicc.
5 g potassium dihydrogen phosphate sicc.
50 g ammonium thiosulphate sicc.
made up with water to 1 l, pH 6.0.

The wedges were then washed under running water for one minute and dried. The density of the wedges were measured before and after treatment. The results are shown in Table 5.

TABLE 5

| Compound No. | Concentration mol/mol AgNO₃ | Density untreated | Density bleached |
|---|---|---|---|
| 1 | $6.9 \cdot 10^{-2}$ | 1.75 | 0.08 |
| 2 | $6.9 \cdot 10^{-2}$ | 1.86 | 0.36 |
| 3 | $7.2 \cdot 10^{-2}$ | 1.74 | 0.24 |
| 4 | $7.0 \cdot 10^{-2}$ | 1.88 | 0.17 |
| 5 | $7.1 \cdot 10^{-2}$ | 1.71 | 0.05 |
| 6 | $6.9 \cdot 10^{-2}$ | 1.77 | 0.06 |
| 7 | $6.9 \cdot 10^{-2}$ | 1.90 | 0.21 |
| 8 | $7.0 \cdot 10^{-2}$ | 2.02 | 0.09 |
| Compar. I | $7.1 \cdot 10^{-2}$ | 2.02 | 2.23 |
| Compar. II | $7.2 \cdot 10^{-2}$ | 2.09 | 2.11 |
| Compar. III | $7.0 \cdot 10^{-2}$ | 1.96 | 2.02 |

Comparison I and Comparison II as in Example 2
Comparison III = 1-phenyl-5-mercaptotetrazole

I claim:
1. Photographic recording material containing at least one light-sensitive silver halide emulsion layer, optionally also other layers and an antifoggant, characterized in that the antifoggant contained therein is a compound corresponding to the following formula I

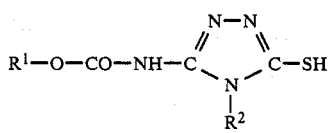

wherein

R$^1$ denotes ethyl, isopropyl, cyclohexyl or allyl or an ethyl or butyl group which is substituted with at least one Cl atom and R$^2$ denotes methyl, ethyl or methoxymethyl.

2. Photographic recording material according to claim 1, characterized in that the compound corresponding to formula I is contained in a light-sensitive silver halide emulsion layer.

3. Photographic recording material according to claim 1, characterized in that the compound corresponding to formula I is contained in a quantity of from $10^{-5}$ to $10^{-2}$ mol per mol of silver halide.

4. Photographic recording material according to claim 1, characterized in that at least one light-sensitive silver halide emulsion layer has a color coupler associated therewith.

* * * * *